(12) United States Patent
Maubru

(10) Patent No.: US 7,258,852 B2
(45) Date of Patent: Aug. 21, 2007

(54) COSMETIC COMPOSITIONS CONTAINING A METHACRYLIC ACID COPOLYMER AND AN OIL, AND USES THEREOF

(75) Inventor: Mireille Maubru, Chatou (FR)

(73) Assignee: L'Oreal S.A., Paris (FR)

( * ) Notice: Subject to any disclaimer, the term of this patent is extended or adjusted under 35 U.S.C. 154(b) by 406 days.

(21) Appl. No.: 10/237,666

(22) Filed: Sep. 10, 2002

(65) Prior Publication Data

US 2003/0108578 A1 Jun. 12, 2003

(30) Foreign Application Priority Data

Sep. 11, 2001 (FR) ................... 01 11743

(51) Int. Cl.
*A61Q 5/02* (2006.01)
*A61Q 5/12* (2006.01)
(52) U.S. Cl. ............... 424/70.11; 424/70.122; 424/70.15; 424/70.16; 424/70.17
(58) Field of Classification Search ............ None
See application file for complete search history.

(56) References Cited

U.S. PATENT DOCUMENTS

| | | |
|---|---|---|
| 2,261,002 A | 10/1941 | Ritter |
| 2,271,378 A | 1/1942 | Searle |
| 2,273,780 A | 2/1942 | Dittmar |
| 2,375,853 A | 5/1945 | Kirby et al. |
| 2,388,614 A | 11/1945 | Kirby et al. |
| 2,454,547 A | 11/1948 | Bock et al. |
| 2,528,378 A | 10/1950 | Mannheimer |
| 2,781,354 A | 2/1957 | Mannheimer |
| 2,961,347 A | 11/1960 | Floyd |
| 3,206,462 A | 9/1965 | McCarty |
| 3,227,615 A | 1/1966 | Korden |
| 3,576,592 A | 4/1971 | Zviak et al. |
| 3,632,559 A | 1/1972 | Matter et al. |
| 3,836,537 A | 9/1974 | Boerwinkle et al. |
| 3,874,870 A | 4/1975 | Green et al. |
| 3,917,817 A | 11/1975 | Vanlerberghe et al |
| 3,929,990 A | 12/1975 | Green et al. |
| 3,966,904 A | 6/1976 | Green et al. |
| 4,001,432 A | 1/1977 | Green et al. |
| 4,005,193 A | 1/1977 | Green et al. |
| 4,013,787 A | 3/1977 | Varlerberghe et al. |
| 4,025,617 A | 5/1977 | Green et al. |
| 4,025,627 A | 5/1977 | Green et al. |
| 4,025,653 A | 5/1977 | Green et al. |
| 4,026,945 A | 5/1977 | Green et al. |
| 4,027,008 A | 5/1977 | Sokol |
| 4,027,020 A | 5/1977 | Green et al. |
| 4,031,307 A | 6/1977 | DeMartino et al. |
| 4,131,576 A | 12/1978 | Iovine et al. |
| 4,172,887 A | 10/1979 | Vanlerberghe et al. |
| 4,223,009 A | 9/1980 | Chakrabarti |
| 4,277,581 A | 7/1981 | Vanlerberghe et al. |
| 4,283,384 A | 8/1981 | Jacquet et al. |
| 4,349,532 A | 9/1982 | Vanlerberghe et al. |
| 4,591,610 A | 5/1986 | Grollier |
| 4,608,250 A | 8/1986 | Jacquet et al. |
| 4,638,822 A | 1/1987 | Grollier et al. |
| 4,693,935 A | 9/1987 | Mazurek |
| 4,719,099 A | 1/1988 | Grollier et al. |
| 4,728,571 A | 3/1988 | Clemens et al. |
| 4,761,273 A | 8/1988 | Grollier et al. |
| 4,839,166 A | 6/1989 | Grollier et al. |
| 4,957,732 A | 9/1990 | Grollier et al. |
| 4,972,037 A | 11/1990 | Garbe et al. |
| 5,037,818 A | 8/1991 | Sime |
| 5,139,037 A | 8/1992 | Grollier et al. |
| 5,196,189 A | 3/1993 | Jacquet et al. |
| 5,275,755 A | 1/1994 | Sebag et al. |
| 5,342,611 A * | 8/1994 | Komori et al. ............ 424/70.1 |
| 5,547,658 A | 8/1996 | Hansenne et al. |
| 5,653,969 A | 8/1997 | Carballada et al. |
| 5,720,964 A | 2/1998 | Murray |
| 5,853,700 A | 12/1998 | Gormley et al. |
| 5,914,103 A | 6/1999 | Armbruster et al. |
| 5,937,866 A | 8/1999 | Magharehi |
| 5,958,392 A | 9/1999 | Grollier et al. |

(Continued)

FOREIGN PATENT DOCUMENTS

DE 41 27 230 2/1993

(Continued)

OTHER PUBLICATIONS

Chemical Abstract XP-002206903 of JP 07-145023, Jun. 6, 1995.

(Continued)

*Primary Examiner*—Jyothsna Venkat
(74) *Attorney, Agent, or Firm*—Finnegan, Henderson, Farabow, Garrett & Dunner, LLP

(57) ABSTRACT

Cosmetic compositions comprising, in a cosmetically acceptable medium, at least one crosslinked methacrylic acid/$C_1$-$C_4$ alkyl acrylate copolymer, at least one oil chosen from synthetic oils, $C_3$-$C_{14}$ acid esters comprising in total less than 20 carbon atoms, and plant oils with a palmitoleic acid content of greater than or equal to 0.2% by weight of the oil. These compositions can be used for washing and/or conditioning keratin materials such as the hair or the skin.

46 Claims, No Drawings

U.S. PATENT DOCUMENTS

| | | | |
|---|---|---|---|
| 5,997,851 A * | 12/1999 | Cox et al. .................. | 424/70.1 |
| 6,007,802 A | 12/1999 | Coffindaffer | |
| 6,106,816 A | 8/2000 | Hitchen | |
| 6,132,705 A | 10/2000 | Schehlmann et al. | |
| 6,165,446 A | 12/2000 | Samain et al. | |
| 6,248,317 B1 | 6/2001 | Snyder et al. | |
| 6,482,394 B1 | 11/2002 | Schehlmann et al. | |
| 6,635,262 B2 | 10/2003 | Jourdan et al. | |
| 6,635,702 B1 * | 10/2003 | Schmucker-Castner et al. .. | 524/291 |
| 2003/0068291 A1 | 4/2003 | Decoster et al. | |

FOREIGN PATENT DOCUMENTS

| | | |
|---|---|---|
| DE | 197 50 520 | 5/1999 |
| EP | 0 761 095 A2 | 3/1977 |
| EP | 0 080 976 | 6/1983 |
| EP | 0 122 324 | 10/1984 |
| EP | 0 337 354 | 10/1989 |
| EP | 0 412 704 | 2/1991 |
| EP | 0 412 707 | 2/1991 |
| EP | 0 457 688 | 11/1991 |
| EP | 0 463 780 | 1/1992 |
| EP | 0 585 152 | 2/1994 |
| EP | 0 761 095 | 3/1997 |
| EP | 1 112 736 | 7/2001 |
| EP | 1 138 315 | 10/2001 |
| EP | 0 970 685 | 6/2005 |
| FR | 1 400 366 | 4/1965 |
| FR | 1 492 597 | 8/1967 |
| FR | 1 583 363 | 10/1969 |
| FR | 2 077 143 | 10/1971 |
| FR | 2 080 759 | 11/1971 |
| FR | 2 162 025 | 7/1973 |
| FR | 2 190 406 | 2/1974 |
| FR | 2 252 840 | 6/1975 |
| FR | 2 270 846 | 12/1975 |
| FR | 2 280 361 | 2/1976 |
| FR | 2 316 271 | 1/1977 |
| FR | 2 320 330 | 3/1977 |
| FR | 2 336 434 | 7/1977 |
| FR | 2 368 508 | 5/1978 |
| FR | 2 383 660 | 10/1978 |
| FR | 2 393 573 | 1/1979 |
| FR | 2 413 907 | 8/1979 |
| FR | 2 470 596 | 8/1981 |
| FR | 2 505 348 | 11/1982 |
| FR | 2 519 863 | 7/1983 |
| FR | 2 542 997 | 9/1984 |
| FR | 2 589 476 | 5/1987 |
| FR | 2 598 611 | 11/1987 |
| FR | 2 641 185 | 8/1990 |
| FR | 2 739 289 | 4/1997 |
| FR | 2 799 956 | 4/2001 |
| FR | 2 816 833 | 5/2002 |
| GB | 1 021 400 | 3/1966 |
| GB | 1 110 240 | 4/1968 |
| GB | 1110240 | 4/1968 |
| HU | 215 636 | 1/1999 |
| JP | 3-34915 | 2/1991 |
| JP | 4-243812 | 8/1992 |
| JP | 8-511272 | 11/1996 |
| JP | 11-507078 | 6/1999 |
| JP | 2000-63248 | 2/2000 |
| JP | 2001-151629 | 6/2001 |
| JP | 2001-172167 | 6/2001 |
| WO | WO93/08787 | 5/1993 |
| WO | WO93/23009 | 11/1993 |
| WO | WO93/23466 | 11/1993 |
| WO | WO95/00578 | 1/1995 |
| WO | WO95/03776 | 2/1995 |
| WO | WO95/09599 | 4/1995 |
| WO | WO97/12588 | 4/1997 |
| WO | WO97/35547 | 10/1997 |
| WO | WO98/03155 | 1/1998 |
| WO | WO 01/76552 | 10/2001 |

OTHER PUBLICATIONS

English language Derwent Abstract of DE 41 27 230, Feb. 18, 1993.
English language Derwent Abstract of FR 1 400 366. Apr. 20, 1965.
English language Derwent Abstract of FR 2 589 476, Jul. 19, 1987.
English language Derwent Abstract of FR 2 739 289, Apr. 4, 1997.
English language Derwent Abstract of FR 2 816 833, May 24, 2002.
English language Patent Abstract of Japan for JP 3-34915, Feb. 14, 1991.
English language Derwent Abstract of JP 2000-63248, Feb. 29, 2000.
English language translation of JP-2001 172167, Jun. 26, 2001.
French Search Report for FR 01 11740, priority application of co-pending U.S. Appl. No. 10/238,003, Title: Cosmetic Compositions Containing a Methacrylic Acid Copolymer, A Silicone and a Cationic Polymer, and Uses Thereof, Filed: Sep. 10, 2002.
French Search Report for FR 01 11742, priority application of co-pending U.S. Appl. No. 10/237,679, Title: Cosmetic Compositions Containing a Methacrylic Acid Copolymer, A Silicone and a Cationic Polymer, and Uses Thereof, Filed: Sep. 10, 2002.
French Search Report for FR 01 11745, priority application of co-pending U.S. Appl. No. 10/237,785, Title: Cosmetic Compositions Containing a Methacrylic Acid Copolymer, A Silicone and a Cationic Polymer, and Uses Thereof, Filed: Sep. 10, 2002.
French Search Report for FR 01 11746, priority application of co-pending U.S. Appl. No. 10/237,873, Title: Cosmetic Compositions Containing a Methacrylic Acid Copolymer, A Silicone and a Cationic Polymer, and Uses Thereof, Filed: Sep. 10, 2002.
Office Action dated Sep. 2, 2005, in co-pending U.S. Appl. No. 10/238,003.
Office Action dated Jun. 21, 2005, in co-pending U.S. Appl. No. 10/238,003.
Office Action dated Jan. 7, 2005, in co-pending U.S. Appl. No. 10/238,003.
Office Action dated Jun. 10, 2004, in co-pending U.S. Appl. No. 10/238,003.
Office Action dated Feb. 4, 2004, in co-pending U.S. Appl. No. 10/238,003.
Office Action dated Nov. 23, 2005, in co-pending U.S. Appl. No. 10/237,679.
Office Action dated May 31,2005, in co-pending U.S. Appl. No. 10/237,679.
Office Action dated Jan. 10, 2005, in co-pending U.S. Appl. No. 10/237,679.
Office Action dated Jun. 14, 2005, in co-pending U.S. Appl. No. 10/237,679.
Office Action dated Nov. 23, 2005, in co-pending U.S. Appl. No. 10/237,873.
Office Action dated Jun. 1, 2005, in co-pending U.S. Appl. No. 10/237,873.
Office Action dated Jan. 10, 2005, in co-pending U.S. Appl. No. 10/237,873.
Todd et al., "Volatile Silicone Fluids For Cosmetic Formulations," *Cosmetics and Toiletries* 91:29-32 (1976).
Co-pending U.S. Appl. No. 10/238,003, Title: Cosmetic Compositions Containing a Methacrylic Acid Copolymer, a Silicone and a Cationic Polymer, and Uses Thereof Inventors: Mireille Maubru et al. U.S. Filing Date: Sep. 10, 2002.
Co-pending U.S. Appl. No. 10/237,679, Title: Cosmetic Compositions Containing a Methacrylic Acid Copolymer, a Silicone and a Cationic Polymer, and Uses Thereof Inventors: Mireille Maubru U.S. Filing Date: Sep. 10, 2002.
Co-pending U.S. Appl. No. 10/237,785, Title: Cosmetic Compositions Containing a Methacrylic Acid Copolymer, a Silicone and a Cationic Polymer, and uses Thereof Inventors: Mireille Maubru U.S. Filing Date: Sep. 10, 2002.

Co-pending U.S. Appl. No. 10/237,873, Title: Cosmetic Compositions Containing a Methacrylic Acid Copolymer an Oil, and Uses Thereof Inventors: Mireille Maubru U.S. Filing Date: Sep. 10, 2002.
Database Chemical Abstracts 'en ligne! retrieved from STN Database accession No. 123:152585 XP002206903 * abrege * & JP 07 145023A (Lion Corp.) Jun. 6, 1995.
M.R. Porter, "Handbook of Surfactants", Blackie & Son Ltd., Glasgow & London, 1991, pp. 116-178.

English language Derwent Abstract of EP 0 080 976, Jun. 8, 1983.
English language Derwent Abstract of FR 2 077 143, Oct. 15, 1971.
English language Derwent Abstract of FR 2 080 759, Nov. 19, 1971.
English language Derwent Abstract of FR 2 320 330, Mar. 4, 1977.
English language Derwent Abstract of FR 2 336 434, Jul. 22, 1977.

* cited by examiner

COSMETIC COMPOSITIONS CONTAINING A METHACRYLIC ACID COPOLYMER AND AN OIL, AND USES THEREOF

The present invention relates to novel cosmetic compositions comprising, in a cosmetically acceptable medium, at least one crosslinked methacrylic acid/$C_1$-$C_4$ alkyl acrylate copolymer, and at least one oil chosen from synthetic oils, $C_3$-$C_{14}$ acid esters comprising in total less than 20 carbon atoms, and plant oils with a palmitoleic acid content of greater than or equal to 0.2% by weight of the oil.

It is well known that hair, which has been sensitized (i.e. damaged and/or brittle) to varying degrees under the action of atmospheric agents or under the action of mechanical or chemical treatments, such as dyes, bleaches and/or permanent-waving, may often be difficult to disentangle and to style, and may lack softness.

It has already been recommended to use conditioners, such as cationic polymers or silicones, in compositions for washing or caring for keratinous material such as the hair, in order to be able to disentangle the hair and to give it softness and flexibility. However, at least one of the cosmetic advantages mentioned above is also unfortunately accompanied, on dried hair, by certain cosmetic effects considered as being undesirable, i.e. lankness of the hairstyle (lack of lightness of the hair) and lack of smoothness (hair not uniform from the root to the tip).

In addition, the use of cationic polymers for this purpose can have various drawbacks. On account of their high affinity for the hair, some of these polymers can become deposited thereon to a large extent during repeated use, and can lead to adverse effects such as an unpleasant, laden (charged or loaded) feel, stiffening of the hair and interfibre adhesion, which has an effect on styling. These drawbacks can be accentuated in the case of fine hair, which lacks liveliness and body.

It has already been proposed to use oils such as plant or animal oils or fatty acid esters as conditioners. However, keratin materials treated with these compositions can usually have an unacceptable greasy feel.

Furthermore, to thicken and stabilize compositions containing insoluble conditioners, stabilizers such as crosslinked acrylic polymers of the Carbopol type are frequently used. However, these stabilizers can have the drawback of reducing the cosmetic performance of shampoos, for example, by making the hair more laden and coarser.

In summary, it is found that the current cosmetic compositions containing oils are not entirely satisfactory.

Certain cosmetic compositions, such as detergent compositions, have been disclosed, containing a copolymer of methacrylic acid and of an alkyl acrylate as a stabilizer or a suspending agent for water-insoluble ingredients such as silicones or fatty substances. Such compositions have been described, for example, in patent application WO 01/76552. The foam qualities and cosmetic properties obtained with these compositions are not yet sufficiently satisfactory.

The inventor has now discovered that the combination of at least one crosslinked methacrylic acid/$C_1$-$C_4$ alkyl acrylate copolymer and at least one particular oil makes it possible to overcome at least one of these drawbacks.

Specifically, it has been found that the use of the said acrylic copolymer in the compositions of the present invention can produce on keratin materials, such as the hair, good cosmetic properties, for example, easy disentangling, and also the introduction of lightness, smoothness, softness and suppleness without having the sensation of a charged feel.

Moreover, the compositions according to the invention can be stable and can have an aesthetic visual appearance. The properties for use (appearance, consistency, abundance of the foam, elimination of the foam) can be satisfactory.

The compositions of the invention, when applied to the skin, such as in the form of a bubble bath or a shower gel, can give an improvement in the softness of the skin.

Thus, according to the present invention, novel cosmetic compositions are now proposed, comprising, in a cosmetically acceptable medium, at least one crosslinked copolymer of methacrylic acid and of a $C_1$-$C_4$ alkyl acrylate, and at least one oil chosen from synthetic oils, $C_3$-$C_{14}$ acid esters comprising in total less than 20 carbon atoms, and plant oils with a palmitoleic acid content of greater than or equal to 0.2% by weight of the oil.

Another aspect of the invention is also the composition as defined above, as well as methods, to give the hair lightness, softness, a smooth feel, and flexibility.

Another aspect of the invention relates to a process for treating keratin materials, such as the hair, characterized in that it comprises applying to the keratin materials cosmetic compositions according to the invention.

According to the present invention, the expression "keratin materials" means the hair, the eyelashes, the eyebrows, the skin, the nails, mucous membranes or the scalp.

Another aspect of the invention relates to the addition of a crosslinked methacrylic acid/$C_1$-$C_4$ alkyl acrylate copolymer in, or for the manufacture of, a cosmetic composition comprising at least one oil as defined below.

The various aspects of the invention will now be detailed. All the meanings and definitions of the compounds used in the present invention given below are valid for all the aspects of the invention.

One of the characteristics of the invention is the presence of at least one crosslinked copolymer of methacrylic acid and of a $C_1$-$C_4$ alkyl acrylate.

The methacrylic acid residue is, for example, in an amount ranging from 20% to 80% by weight and further, for example, from 25% to 70% by weight and even further, for example, from 35% to 60% by weight relative to the total weight of the copolymer.

The alkyl acrylate residue is, for example, in an amount ranging from 15% to 80% by weight and further, for example, from 25% to 75% by weight and even further, for example, from 40% to 65% by weight relative to the total weight of the copolymer. It can be chosen from methyl acrylate, ethyl acrylate and butyl acrylate residues.

This copolymer is partially or totally crosslinked with at least one standard crosslinking agent. The crosslinking agents are, for example, polyunsaturated compounds, such as ethylenically polyunsaturated compounds. These compounds are, for example, chosen from polyalkenyl ethers of sucrose and of polyols, diallyl phthalates, divinylbenzene, allyl (meth)acrylate, ethylene glycol di(meth)acrylate, methylenebisacrylamide, trimethylolpropane tri(meth)acrylate, diallyl itaconate, diallyl fumarate, diallyl maleate, zinc (meth)acrylate, and derivatives of castor oil and of polyols produced from unsaturated carboxylic acids.

Crosslinking agents that may also be used include, for example, unsaturated monomeric compounds comprising a reactive group capable of reacting with an unsaturation to form a crosslinked copolymer.

The content of the crosslinking agent generally ranges, for example, from 0.01% to 5% by weight and further, for example, from 0.03% to 3% by weight and even further, for example, from 0.05% to 1% by weight relative to the total weight of the copolymer.

According to one embodiment of the present invention, the copolymer of the invention may be, for example, in the form of a dispersion in water. The number-average size of the copolymer particles in the dispersion is generally, for example, from 10 to 500 nm, as measured by appropriate means known to those skilled in the art, and further, for example, from 20 to 200 nm and even further, for example, from 50 to 150 nm.

These copolymers are described, for example, in application WO 01/76552.

Use can, for example, be made of the crosslinked methacrylic acid/ethyl acrylate copolymer in the form of an aqueous 30% dispersion manufactured and sold under the name Carbopol Aqua SF-1 by the company Noveon.

The copolymer concentration is generally, for example, from 0.01% to 10% by weight relative to the total weight of the composition and further, for example, from 0.1% to 5% by weight relative to the total weight of the composition.

The synthetic oils are, for example, polyolefins, such as poly-α-olefins and further, for example:

of hydrogenated or non-hydrogenated polybutene type, and, for example, hydrogenated or non-hydrogenated polyisobutene.

Isobutylene oligomers with molar weight of less than 1000 and mixtures thereof with polyisobutylenes with a molar weight of greater than 1000 and such as from 1000 to 15000 can, for example, be used.

As examples of poly-α-olefins that may be used in the context of the present invention, mention may be made, for example, of the polyisobutenes sold under the name Permethyl 99 A, 101 A, 102 A, 104 A (n=16) and 106 A (n=38) by the company Presperse Inc., and the products sold under the name Arlamol AD (n=3) by the company ICI (n denoting the degree of polymerization), of hydrogenated or non-hydrogenated polydecene type.

Such products are sold, for example, under the names Ethylflo by the company Ethyl Corp. and Arlamol PAO by the company ICI.

The plant oils are, for example, chosen from avocado oils, jojoba oils, olive oils and apricot oils, and transesterified plant oils.

The esters that may be used according to the invention are chosen, for example, from esters of saturated and unsaturated, linear and branched $C_3$-$C_{14}$ aliphatic mono-, di- and tricarboxylic acids and of saturated and unsaturated, linear and branched $C_1$-$C_{16}$ aliphatic monoalcohols and polyols, the total carbon number being less than or equal to 20.

Among the esters according to the invention that may be mentioned are cetyl lactate, $C_{12}$-$C_{15}$ alkyl lactate, lauryl lactate, oleyl lactate, $C_1$-$C_5$ alkyl myristates such as isopropyl myristate and butyl myristate, hexyl laurate, isononyl isononate, and isodecyl neopentanoate.

The at least one oil can, for example, be used in an amount ranging from 0.01% to 20% by weight relative to the total weight of the composition. For example, this amount ranges from 0.05% to 15% by weight relative to the total weight of the composition and, further, for example, from 0.1% to 10% by weight relative to the total weight of the composition.

According to one embodiment of the invention, the composition further comprises at least one polymer chosen from cationic and amphoteric polymers.

The cationic polymers that may be used in accordance with the present invention may be chosen from any of those already known as improving the cosmetic properties of the hair, for example, those described in patent application EP-A-0 337 354 and in French patent applications FR-A-2 270 846, 2 383 660, 2 598 611, 2 470 596 and 2 519 863.

As used herein, "cationic polymer" refers to polymers chosen from polymers comprising at least one cationic group and polymers comprising at least one group which can be ionized to form cationic groups.

The cationic polymers may, for example, be chosen from those comprising units comprising primary, secondary, tertiary and/or quaternary amine groups that may either form part of the main polymer chain, or may be borne by a side substituent that is directly attached to the main chain.

The cationic polymers used generally have a number-average or weight-average molar mass ranging from 500 to $5\times10^6$ and, for example, from $10^3$ to $3\times10^6$.

Among the cationic polymers that may be mentioned, for example, are polymers of polyamine, polymers of polyamino amide and polymers of polyquaternary ammonium. These polymers are known in the art.

The polymers of polyamine, polymers of polyamino amide and polymers of polyquaternary ammonium that may be used in accordance with the present invention, and that may be mentioned, for example, are those described in French Patent Nos. 2 505 348 and 2 542 997. Among these polymers, mention may be made of:

(1) homopolymers or copolymers derived from acrylic or methacrylic esters or amides and comprising at least one of the units of the following formulae:

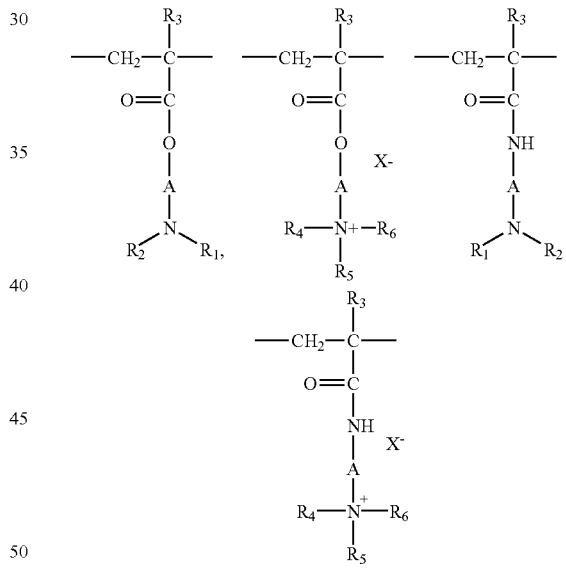

in which:

$R_3$, which may be identical or different, is chosen from a hydrogen atom and a $CH_3$ radical;

A, which may be identical or different, is chosen from linear and branched alkyl groups of 1 to 6 carbon atoms, such as 2 or 3 carbon atoms, and hydroxyalkyl groups of 1 to 4 carbon atoms;

$R_4$, $R_5$ and $R_6$, which may be identical or different, are chosen from alkyl groups comprising from 1 to 18 carbon atoms and benzyl radicals, such as alkyl groups comprising from 1 to 6 carbon atoms;

$R_1$ and $R_2$, which may be identical or different, are chosen from a hydrogen atom and alkyl groups comprising from 1 to 6 carbon atoms, and for example, methyl and ethyl groups;

X⁻ is an anion derived from an inorganic or organic acid, such as a methosulphate anion or an anion chosen from halides such as chloride or bromide.

Copolymers of family (1) can also comprise at least one unit derived from comonomers, which may be chosen from the family of acrylamides, methacrylamides, diacetone acrylamides, acrylamides and methacrylamides substituted on the nitrogen with at least one group chosen from lower ($C_1$-$C_4$) alkyls, acrylic acids, methacrylic acids, acrylic esters, methacrylic esters, vinyllactams, such as vinylpyrrolidone and vinylcaprolactam, and vinyl esters.

Thus, among these copolymers of family (1), mention may be made of:

the copolymers of acrylamide and of dimethylaminoethyl methacrylate quaternized with dimethyl sulphate or with a dimethyl halide, such as the product sold under the name Hercofloc by the company Hercules, the copolymers of acrylamide and of methacryloyloxyethyltrimethylammonium chloride described, for example, in patent application EP-A-080 976 and sold under the name Bina Quat P 100 by the company Ciba Geigy, the copolymer of acrylamide and of methacryloyloxyethyltrimethylammonium methosulphate sold under the name Reten by the company Hercules, quaternized or non-quaternized vinylpyrrolidone/dialkylaminoalkyl acrylate or methacrylate copolymers, such as the products sold under the name "Gafquat" by the company ISP, such as "Gafquat 734" or "Gafquat 755" or the products known as "Copolymer 845, 958 and 937". These polymers are described in detail in French Patent Nos. 2 077 143 and 2 393 573, dimethylaminoethyl methacrylate/vinylcaprolactam/vinylpyrrolidone terpolymers, such as the product sold under the name Gaffix VC 713 by the company ISP, vinylpyrrolidone/methacrylamidopropyldimethylamine copolymers sold, for example, under the name Styleze CC 10 by ISP, and quaternized vinylpyrrolidone/dimethylaminopropylmethacrylamide copolymers, such as the product sold under the name "Gafquat HS 100" by the company ISP.

(2)cationic polysaccharides, such as celluloses and cationic galactomannan gums. Among the

|
cationic polysaccharides that may be mentioned, for example, are cellulose ether derivatives comprising quaternary ammonium groups, cationic cellulose copolymers or cellulose derivatives grafted with a water-soluble quaternary ammonium monomer and cationic galactomannan gums.

The cellulose ether derivatives comprising quaternary ammonium groups, which are described in French Patent No. 1 492 597, and, for example, the polymers sold under the names "JR" (JR 400, JR 125 or JR 30M) or "LR" (LR 400 or LR 30M) by the company NALCO. These polymers are also defined in the CTFA dictionary as hydroxyethylcellulose quaternary ammoniums that have reacted with an epoxide substituted with a trimethylammonium group.

The cationic cellulose copolymers or cellulose derivatives grafted with a water-soluble quaternary ammonium monomer are described, for example, in U.S. Pat. No. 4,131,576, such as hydroxyalkylcelluloses, for instance hydroxymethylcelluloses, hydroxyethylcelluloses and hydroxypropylcelluloses grafted, for example, with a salt chosen from methacryloylethyltrimethylammonium salts, methacrylamidopropyltrimethylammonium salts and dimethyldiallylammonium salts.

The products sold corresponding to this definition are, for example, the products sold under the names "Celquat L 200" and "Celquat H 100" by the company National Starch.

The cationic galactomannan gums are described, for example, in U.S. Pat. Nos. 3,589,578 and 4,031,307, such as guar gums comprising trialkylammonium cationic groups. For example, guar gums modified with a salt (e.g. chloride) of 2,3-epoxypropyltrimethylammonium may be used.

Such products are sold, for example, under the trade names Jaguar C13 S, Jaguar C15, Jaguar C17 or Jaguar C162 by the company Meyhall.

(3)polymers comprising piperazinyl units and divalent alkylene or hydroxyalkylene radicals comprising straight or branched chains, optionally interrupted by at least one atom chosen from oxygen, sulphur and nitrogen atoms or by at least one aromatic or heterocyclic ring, as well as at least one of the oxidation and/or quaternization products of these polymers. Such polymers are described, for example, in French Patent Nos. 2 162 025 and 2 280 361;

(4)water-soluble polyamino amides prepared, for example, by polycondensation of an acidic compound, with a polyamine; these polyamino amides being crosslinked with an epihalohydrin, a diepoxide, a dianhydride, an unsaturated dianhydride, a bis-unsaturated derivative, a bis-halohydrin, a bis-azetidinium, a bis-haloacyldiamine, a bis-alkyl halide or with an oligomer resulting from the reaction of a difunctional compound which is reactive with a bis-halohydrin, a bis-azetidinium, a bis-haloacyldiamine, a bis-alkyl halide, an epihalohydrin, a diepoxide or a bis-unsaturated derivative. The crosslinking agent can be used in proportions ranging from 0.025 to 0.35 mol per amine group of the polyamino amide. These polyamino amides can be alkylated or, if they comprise at least one tertiary amine function, they can be quaternized. Such polymers are described, for example, in French Patent Nos. 2 252 840 and 2 368 508;

(5)polyaminoamide derivatives resulting from the condensation of polyalkylene polyamines with polycarboxylic acids followed by alkylation with difunctional agents. Mention may be made, for example, of adipic acid/dialkylaminohydroxyalkyldialkylenetriamine polymers in which the alkyl radical comprises from 1 to 4 carbon atoms and such as methyl, ethyl or propyl. Such polymers are described, for example, in French Patent No. 1 583 363.

Among these derivatives, mention may be made, for example, of the adipic acid/dimethylaminohydroxypropyl/diethylenetriamine polymers sold under the name "Cartaretine F, F4 or F8" by the company Sandoz.

(6)polymers obtained by reaction of a polyalkylene polyamine comprising two primary amine groups and at least one secondary amine group with a dicarboxylic acid chosen from diglycolic acids and saturated aliphatic dicarboxylic acids comprising from 3 to 8 carbon atoms. The molar ratio between the polyalkylene polyamine and the dicarboxylic acid may range from 0.8:1 to 1.4:1; the polyamino amide resulting therefrom may be reacted with epichlorohydrin in a molar ratio of epichlorohydrin relative to the secondary amine group of the polyamino amide ranging from 0.5:1 to 1.8:1. Such polymers are described, for example, in U.S. Pat. Nos. 3,227,615 and 2,961,347.

Other non-limiting examples of such derivatives include the adipic acid/epoxypropyl/diethylenetriamine copolymers sold, for example, under the name "Hercosett 57" by the company Hercules Inc. or under the name of "PD 170" or Delsette 101" by the company Hercules.

(7) cyclopolymers of alkyldiallylamine or of dialkyldiallylammonium, such as the homopolymers or copolymers comprising, as main constituent of the chain, at least one unit corresponding to formula (I) or (I'):

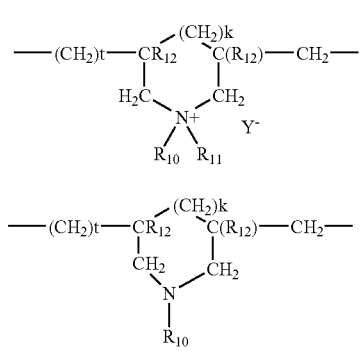

in which k and t are equal to 0 or 1, the sum k+t being equal to 1;

$R_{12}$ is chosen from a hydrogen atom and a methyl radical;

$R_{10}$ and $R_{11}$, which may be identical or different, are chosen from alkyl groups comprising from 1 to 6 carbon atoms, hydroxyalkyl groups in which the alkyl group, for example, comprises from 1 to 5 carbon atoms, and lower $C_1$-$C_4$ amidoalkyl groups, or $R_{10}$ and $R_{11}$ can denote, together with the nitrogen atom to which they are attached, heterocyclic groups such as piperidyl or morpholinyl; $Y^-$ is an anion such as bromide, chloride, acetate, borate, citrate, tartrate, bisulphate, bisulphite, sulphate and phosphate. These polymers are described, for example, in French Patent No. 2 080 759 and in its Certificate of Addition 2 190 406.

In one embodiment, $R_{10}$ and $R_{11}$, which may be identical or different, are, for example, chosen from alkyl groups comprising from 1 to 4 carbon atoms.

Among the polymers defined above, mention may be made, for example, of the dimethyidiallylammonium chloride homopolymer sold under the name "Merquat 100" by the company Nalco (its homologues of low weight-average molecular mass) and copolymers of diallyidimethylammonium chloride and of acrylamide.

(8) The quaternary diammonium polymers comprising repeating units corresponding to the formula (II):

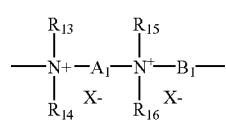

in which:

$R_{13}$, $R_{14}$, $R_{15}$ and $R_{16}$, which may be identical or different, are chosen from aliphatic, alicyclic and arylaliphatic radicals comprising from 1 to 20 carbon atoms and from lower hydroxyalkylaliphatic radicals, or $R_{13}$, $R_{14}$, $R_{15}$ and $R_{16}$, together or separately, constitute, with the nitrogen atoms to which they are attached, heterocycles optionally comprising a second hetero atom other than nitrogen, or $R_{13}$, $R_{14}$, $R_{15}$ and $R_{16}$ are chosen from linear and branched $C_1$-$C_6$ alkyl radicals substituted with at least one group chosen from nitrile, ester, acyl and amide groups and groups of —CO—O—$R_{17}$-D and —CO—NH—$R_{17}$-D, wherein $R_{17}$ is chosen from alkylene groups and D is chosen from quaternary ammonium groups;

$A_1$ and $B_1$, which may be identical or different, are chosen from linear and branched, saturated and unsaturated polymethylene groups comprising from 2 to 20 carbon atoms. The polymethylene groups may comprise, linked to or intercalated in the main chain, at least one entity chosen from aromatic rings, oxygen and sulphur atoms and sulphoxide, sulphone, disulphide, amino, alkylamino, hydroxyl, quaternary ammonium, ureido, amide and ester groups; and $X^-$ is an anion chosen from anions derived from inorganic acids and organic acids.

$A_1$, $R_{13}$ and $R_{15}$ may optionally form, with the two nitrogen atoms to which they are attached, a piperazine ring; in addition, if $A_1$ is a radical chosen from linear and branched, saturated and unsaturated alkylene and hydroxyalkylene radicals, $B_1$ can also denote a group $(CH_2)_n$—CO-D-OC—$(CH_2)_n$—, wherein n ranges from 1 to 100, such as from 1 to 50, D is chosen from:

a) a glycol residue of formula: —O-Z-O—, where Z is chosen from linear and branched hydrocarbon-based radicals and a group corresponding to one of the following formulae:

—(CH$_2$—CH$_2$—O)$_x$—CH$_2$—CH$_2$—

—[CH$_2$—CH(CH$_3$)—O]$_y$—CH$_2$—CH(CH$_3$)— wherein x and y, which may be identical or different, are each an integer ranging from 1 to 4, representing a defined and unique degree of polymerization or any number ranging from 1 to 4 representing an average degree of polymerization;

b) a bis-secondary diamine residue such as a piperazine derivative;

c) a bis-primary diamine residue of formula: —NH—Y—NH—, wherein Y is chosen from linear and branched hydrocarbon radicals, and the divalent radical —CH$_2$—CH$_2$—S—S—CH$_2$—CH$_2$—; and d) a ureylene group of formula: —NH—CO—NH—.

For example, $X^-$ is an anion such as chloride or bromide.

These polymers may have a number-average molecular mass ranging from 1000 to 100,000.

These polymers are described, for example, in French Patent Nos. 2 320 330, 2 270 846, 2 316 271, 2 336 434 and 2 413 907 and U.S. Pat. Nos. 2,273,780, 2,375,853, 2,388, 614, 2,454,547, 3,206,462, 2,261,002, 2,271,378, 3,874,870, 4,001,432, 3,929,990, 3,966,904, 4,005,193, 4,025,617, 4,025,627, 4,025,653, 4,026,945 and 4,027,020.

Further, according to the present invention, polymers can comprise repeating units corresponding to the formula (a):

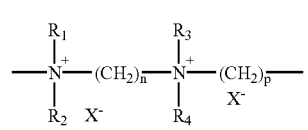

in which $R_1$, $R_2$, $R_3$ and $R_4$, which may be identical or different, are chosen from alkyl and hydroxyalkyl radicals comprising from 1 to 4 carbon atoms, n and p, which may be identical or different, are integers ranging from 2 to 20, and $X^-$ is an anion chosen from anions derived from inorganic acids and organic acids.

One compound of formula (a), for example, is the one for which $R_1$, $R_2$, $R_3$ and $R_4$ are each a methyl radical and n=3, p=6 and X=Cl, which is known as Hexadimethrine chloride according to the INCI (CTFA) nomenclature.

(9) polyquaternary ammonium polymers comprising repeating units of formula (III):

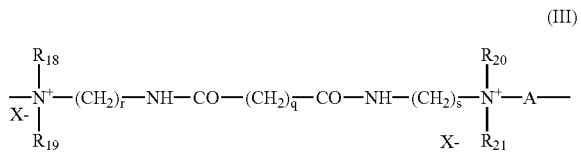

in which:

$R_{18}$, $R_{19}$, $R_{20}$ and $R_{21}$, which may be identical or different, are chosen from a hydrogen atom and methyl, ethyl, propyl, β-hydroxyethyl, β-hydroxypropyl and —$CH_2CH_2$(OCH$_2$CH$_2$)$_p$OH radicals, wherein p is equal to 0 or to an integer ranging from 1 to 6, with the proviso that $R_{18}$, $R_{19}$, $R_{20}$ and $R_{21}$ do not simultaneously represent a hydrogen atom, r and s, which may be identical or different, are each an integer ranging from 1 to 6, q is equal to 0 or to an integer ranging from 1 to 34, $X^-$ is an anion such as a halide, A is chosen from divalent radicals, such as —$CH_2$—$CH_2$—O—$CH_2$—$CH_2$—.

Such polymers are described, for example, in patent application EP-A-122 324.

Among these polymers, mention may be made, for example, of "Mirapol® A 15", "Mirapol® AD1", "Mirapol® AZ1" and "Mirapol® 175" sold by the company Mirapol.

(10) quaternary polymers of vinylpyrrolidone and of vinylimidazole, such as the products sold under the names Luviquat® FC 905, FC 550 and FC 370 by the company BASF.

(11) polyamines, for instance Polyquart® H sold by Cognis, referenced under the name "Polyethylene glycol (15) tallow polyamine" in the CTFA dictionary.

(12) Crosslinked methacryloyloxy($C_1$-$C_4$)alkyltri($C_1$-$C_4$)alkylammonium salt polymers such as the polymers obtained by homopolymerization of dimethylaminoethyl methacrylate quaternized with methyl chloride, or by copolymerization of acrylamide with dimethylaminoethyl methacrylate quaternized with methyl chloride, the homo- or copolymerization being followed by crosslinking with a compound comprising olefinic unsaturation, such as methylenebisacrylamide. In one embodiment, a crosslinked acrylamide/methacryloyloxyethyltrimethylammonium chloride copolymer (20/80 by weight) in the form of a dispersion comprising 50% by weight of the said copolymer in mineral oil can be used. This dispersion is sold under the name "Salcare® SC 92" by the company Allied Colloids. In another embodiment, a crosslinked methacryloyloxyethyltrimethylammonium chloride homopolymer comprising about 50% by weight of the homopolymer in mineral oil or in a liquid ester can be used. These dispersions are sold under the names "Salcare® SC 95" and "Salcare® SC 96" by the company Allied Colloids.

Other cationic polymers, which can be used in the context of the invention, are chosen from cationic proteins and cationic protein hydrolysates, polyalkyleneimines, such as polyethyleneimines, polymers comprising units chosen from vinylpyridine units and vinylpyridinium units, condensates of polyamines and of epichlorohydrin, quaternary polyureylenes and chitin derivatives.

Among all the cationic polymers that may be used in the context of the present invention, non-limiting examples include quaternary cellulose ether derivatives, such as the products sold under the name "JR 400" by the company Nalco, cationic cyclopolymers, such as the dimethyldiallylammonium chloride homopolymers or copolymers sold under the names "Merquat 100", "Merquat 550" and "Merquat S" by the company Nalco, quaternary polymers of vinylpyrrolidone and of vinylimidazole, crosslinked homopolymers or copolymers of methacryloyloxy($C_1$-$C_4$)alkyltri($C_1$-$C_4$)alkylammonium salts, and mixtures thereof.

The amphoteric polymers, which may be used in accordance with the present invention, may be chosen from polymers comprising units K and M randomly distributed in the polymer chain, in which K is a unit derived from a monomer comprising at least one basic nitrogen atom and M is a unit derived from an acidic monomer comprising at least one carboxylic or sulphonic group, or K and M may be chosen from groups derived from zwitterionic carboxybetaine or sulphobetaine monomers.

K and M may also be chosen from a cationic polymer chain comprising at least one group chosen from primary, secondary, tertiary and quaternary amine groups, in which at least one of the amine groups bears a carboxylic or sulphonic group linked via a hydrocarbon-based radical, or K and M can form part of a chain of a polymer comprising an α,β-dicarboxylic ethylene unit in which one of the carboxylic groups has been made to react with a polyamine comprising at least one amine chosen from primary and secondary amine groups.

The amphoteric polymers corresponding to the above definition, for example, are chosen from the following polymers:

(1) polymers resulting from the copolymerization of at least one monomer derived from a vinyl compound bearing a carboxylic group such as acrylic acid, methacrylic acid, maleic acid, α-chloroacrylic acid, and at least one basic monomer derived from a substituted vinyl compound comprising at least one basic atom, such as dialkylaminoalkyl methacrylate and acrylate, dialkylaminoalkylmethacrylamide and -acrylamide. Such compounds are described, for example, in U.S. Pat. No. 3,836,537.

Mention may also be made of the sodium acrylate/acrylamidopropyltrimethylammonium chloride copolymer sold under the name Polyquart KE 3033 by the company Cognis. The vinyl compound may also be a dialkyldiallylammonium salt such as dimethyldiallylammonium chloride. The copolymers of acrylic acid and of the latter monomer are sold under the names Merquat 280, Merquat 295 and Merquat Plus 3330 by the company Nalco.

(2) polymers comprising units derived from:

a) at least one monomer chosen from acrylamides and methacrylamides substituted on the nitrogen with an alkyl radical, b) at least one acidic comonomer comprising at least one reactive carboxylic group, and c) at least one basic comonomer such as esters comprising substituents chosen from primary, secondary, tertiary and quaternary amine substituents of acrylic and methacrylic acids and the product of quaternization of dimethylaminoethyl methacrylate with dimethyl or diethyl sulphate.

In one embodiment, the N-substituted acrylamides or methacrylamides according to the invention are, for example, groups in which the alkyl radicals comprise from 2 to 12 carbon atoms, such as N-ethylacrylamide, N-tert-butylacrylamide, N-tert-octylacrylamide, N-octylacrylamide, N-decylacrylamide, N-dodecylacrylamide and the corresponding methacrylamides.

The acidic comonomers are chosen, for example, from acrylic acids, methacrylic acids, crotonic acids, itaconic acids, maleic acids and fumaric acids and alkyl monoesters, comprising 1 to 4 carbon atoms, of maleic or fumaric acids or anhydrides.

The basic comonomers are chosen, for example, from aminoethyl, butylaminoethyl, N,N'-dimethylaminoethyl and N-tert-butylaminoethyl methacrylates.

The copolymers having the CTFA (4th edition, 1991) name octylacrylamide/acrylates/butylaminoethyl methacrylate copolymer, such as the products sold under the name Amphomer or Lovocryl 47 by the company National Starch, can, for example, be used.

(3) crosslinked and alkylated polyamino amides partially or totally derived from polyamino amides of general formula:

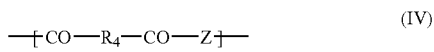

(IV)

in which $R_4$ is chosen from a divalent radical derived from saturated dicarboxylic acid, mono- and dicarboxylic aliphatic acids comprising an ethylenic double bond, an ester of a lower alkanol, comprising from 1 to 6 carbon atoms, of these acids and a radical derived from the addition of any one of the acids to amines chosen from bis(primary) and bis(secondary) amines, and Z is chosen from bis(primary), mono- and bis(secondary) polyalkylene-polyamine radicals and, for example, Z represents:

a) in proportions of from 60 to 100 mol %, the radical

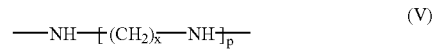

(V)

wherein x=2 and p=2 or 3, or x=3 and p=2, this radical being derived from a compound chosen from diethylenetriamine, triethylenetetraamine and dipropylenetriamine;

b) in proportions of from 0 to 40 mol %, the radical (V) above in which x=2 and p=1 and which is derived from a compound chosen from ethylenediamine and piperazine:

c) in proportions of from 0 to 20 mol %, the —NH—$(CH_2)_6$—NH— radical, which is derived from hexamethylenediamine, these polyamino amides can be crosslinked by addition of a difunctional crosslinking agent chosen from epihalohydrins, diepoxides, dianhydrides and bis-unsaturated derivatives, using from 0.025 to 0.35 mol of crosslinking agent per amine group of the polyamino amide and alkylated by the action of acrylic acid, chloroacetic acid or an alkane sultone, or salts thereof.

In one embodiment, the saturated carboxylic acids are, for example, chosen from acids comprising 6 to 10 carbon atoms, such as adipic acid, 2,2,4-trimethyladipic acid and 2,4,4-trimethyladipic acid, terephthalic acid and acids comprising an ethylenic double bond, such as acrylic acid, methacrylic acid and itaconic acid.

The alkane sultones used in the alkylation are chosen, for example, from propane sultone and butane sultone, and the salts of the alkylating agents can be chosen, for example, from sodium and potassium salts.

(4) polymers comprising zwitterionic units of formula:

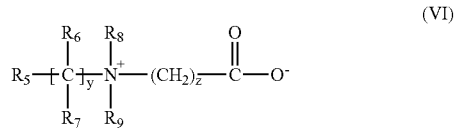

(VI)

in which $R_5$ is chosen from polymerizable unsaturated groups, such as acrylate, methacrylate, acrylamide and methacrylamide groups, y and z, which may be identical or different, are chosen from integers from 1 to 3, $R_6$ and $R_7$, which may be identical or different, are chosen from a hydrogen atom, methyl, ethyl and propyl groups, $R_8$ and $R_9$, which may be identical or different, are chosen from a hydrogen atom and alkyl radicals such that the sum of the carbon atoms in $R_8$ and $R_9$ does not exceed 10.

The polymers comprising such units can also comprise units derived from non-zwitterionic monomers such as monomers chosen from dimethyl and diethylaminoethyl acrylates and methacrylates, alkyl acrylates, methacrylates, acrylamides, methacrylamides and vinyl acetate.

By way of example, mention may be made of the copolymer of butyl methacrylate/d imethylcarboxymethylammonioethyl methacrylate.

(5) polymers derived from chitosan comprising monomer units corresponding to formulae (VII), (VIII) and (IX) below:

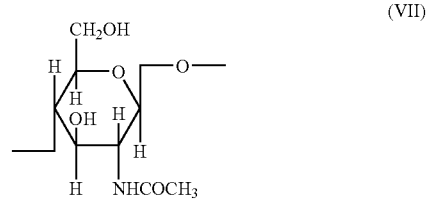

(VII)

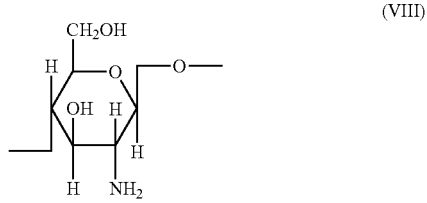

(VIII)

-continued

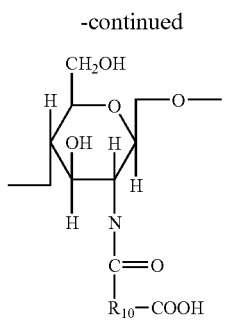
(IX)

the unit (X) being present in proportions ranging from 0 to 30%, the unit (XI) in proportions ranging from 5% to 50% and the unit (XII) in proportions ranging from 30% to 90%, and wherein in the unit (XII), $R_{10}$ is a radical of formula:

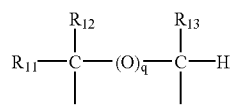

wherein q is equal to 0 or 1;

if q=0, $R_{11}$, $R_{12}$ and $R_{13}$, which may be identical or different, are chosen from a hydrogen atom, methyl, hydroxyl, acetoxy and amino residues, monoalkylamine residues and dialkylamine residues, which are optionally interrupted by at least one nitrogen atom and/or optionally substituted with at least one group chosen from amine, hydroxyl, carboxyl, alkylthio and sulphonic groups, and alkylthio residues in which the alkyl group bears an amino residue, at least one of the radicals $R_{11}$, $R_{12}$ and $R_{13}$ being, in this case, a hydrogen atom;

or, if q=1, $R_{11}$, $R_{12}$ and $R_{13}$, which may be identical or different, are each chosen from a hydrogen atom, and the salts formed by these compounds with bases or acids.

(6) polymers derived from the N-carboxyalkylation of chitosan, such as N-carboxymethylchitosan and N-carboxybutylchitosan.

(7) polymers corresponding to the general formula (X) as described, for example, in French Patent No. 1 400 366:

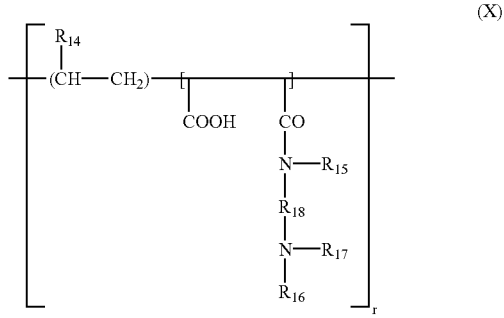
(X)

in which $R_{14}$ is chosen from a hydrogen atom, and $CH_3O$, $CH_3CH_2O$ and phenyl radicals, $R_{15}$ is chosen from a hydrogen atom and lower alkyl radicals such as methyl and ethyl, $R_{16}$ is chosen from a hydrogen atom and lower alkyl radicals such as methyl and ethyl, $R_{17}$ is chosen from lower alkyl radicals such as methyl and ethyl radicals corresponding to the formula: —$R_{18}$—N$(R_{16})_2$, wherein $R_{18}$ is chosen from —$CH_2$—$CH_2$—, —$CH_2$—$CH_2$—$CH_2$— and —$CH_2$—$CH(CH_3)$— groups, and $R_{16}$ is chosen from a hydrogen atom and lower alkyl radicals such as methyl and ethyl, and the higher homologues of these radicals comprising up to 6 carbon atoms, r is chosen such that the number-average molecular weight of said polymer ranges from 500 to 6,000,000, such as from 1,000 to 1,000,000.

(8) amphoteric polymers of the type -D-X-D-X— chosen from:

a) polymers obtained by the action of chloroacetic acid or sodium chloroacetate on compounds comprising at least one unit of formula:

-D-X-D-X-D- (XI)

wherein D is a radical

and X is chosen from the symbols E and E', wherein E and E', which may be identical or different, are chosen from divalent alkylene radicals comprising at least one chain chosen from straight and branched chains comprising up to 7 carbon atoms in the main chain, wherein said divalent alkylene radicals are optionally substituted with at least one hydroxyl group. E or E' can additionally comprise at least one atom chosen from oxygen, nitrogen and sulphur atoms, and 1 to 3 rings chosen from aromatic and heterocyclic rings. The oxygen, nitrogen and sulphur atoms can be present in the form of at least one group chosen from ether, thioether, sulphoxide, sulphone, sulphonium, alkylamine, alkenylamine, hydroxyl, benzylamine, amine oxide, quaternary ammonium, amide, imide, alcohol, ester and urethane groups;

b) polymers of formula:

-D-X-D-X— (XII)

wherein D is a radical

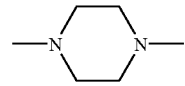

and X is chosen from the symbols E and E' and wherein at least one X is chosen from E'; E having the meaning given above and E' being chosen from divalent alkylene radicals comprising at least one chain chosen from straight and branched chains comprising up to 7 carbon atoms in the main chain, wherein said divalent alkylene radicals are optionally substituted with at least one hydroxyl radical. E' can also comprise at least one nitrogen atom substituted with an alkyl chain, which is optionally interrupted by an oxygen atom, wherein said alkyl chain comprises at least one functional group chosen from carboxyl functional groups and hydroxyl functional groups, and wherein the alkyl chain is betainized by reaction with a reactant chosen from chloroacetic acid and sodium chloroacetate.

(9)($C_1$-$C_5$)alkyl vinyl ether/maleic anhydride copolymers partially modified by semiamidation with an N,N-dialkylaminoalkylamine such as N,N-dimethylaminopropylamine or by semiesterification with an N,N-dialkanolamine. These copolymers can also comprise other vinyl comonomers such as vinylcaprolactam.

The amphoteric polymers according to the invention are, in certain embodiments, those of family (1).

According to the invention, the at least one polymer chosen from cationic and amphoteric polymers may be present in an amount ranging from 0.001% to 20% by weight, such as from 0.01% to 10% by weight and further such as from 0.1% to 5% by weight relative to the total weight of the composition.

The compositions of the invention can also comprise at least one surfactant, which is generally present in an amount ranging, for example, from 0.01% to 50% by weight, such as from 0.1% to 40% by weight and further such as from 0.5% and 30% by weight relative to the total weight of the composition.

The at least one surfactant may be chosen from anionic, amphoteric, nonionic and cationic surfactants.

The at least one surfactant that is suitable for carrying out the present invention is, for example, chosen from:

(i) Anionic surfactants:

As examples of anionic surfactants, which can be used, alone or as mixtures, in the context of the present invention, mention may be made, for example, of salts (such as alkaline salts, for example, sodium salts, ammonium salts, amine salts, amino alcohol salts or magnesium salts) of the following compounds: alkyl sulphates, alkyl ether sulphates, alkylamidoether sulphates, alkylarylpolyether sulphates, monoglyceride sulphates; alkyl sulphonates, alkyl phosphates, alkylamide sulphonates, alkylaryl sulphonates, α-olefin sulphonates, paraffin sulphonates; alkyl sulphosuccinates, alkyl ether sulphosuccinates, alkylamide sulphosuccinates; alkyl sulphosuccinamates; alkyl sulphoacetates; alkyl ether phosphates; acyl sarcosinates; acyl isethionates and N-acyltaurates. The alkyl or acyl radical of all of these various compounds, for example, comprises from 8 to 24 carbon atoms, and the aryl radical is chosen from phenyl and benzyl groups. Among the anionic surfactants, which can also be used, mention may also be made of fatty acid salts such as the salts of oleic, ricinoleic, palmitic and stearic acids, coconut oil acid or hydrogenated coconut oil acid; acyl lactylates in which the acyl radical comprises from 8 to 20 carbon atoms. Weakly anionic surfactants can also be used, such as alkyl-D-galactosiduronic acids and their salts, as well as polyoxyalkylenated ($C_6$-$C_{24}$) alkyl ether carboxylic acids, polyoxyalkylenated ($C_6$-$C_{24}$) alkylaryl ether carboxylic acids, polyoxyalkylenated ($C_6$-$C_{24}$) alkylamido ether carboxylic acids and their salts, for example, those comprising from 2 to 50 ethylene oxide groups, and mixtures thereof.

Among the anionic surfactants, for example, alkyl sulphate salts and alkyl ether sulphate salts and mixtures thereof can be used.

(ii) Nonionic surfactants:

The nonionic surfactants are compounds that are well known (see, for example, in this respect "*Handbook of Surfactants*" by M. R. Porter, published by Blackie & Son (Glasgow and London), 1991, pp. 116-178). They can be chosen, for example, from polyethoxylated, polypropoxylated and polyglycerolated fatty acids, alkylphenols, α-diols and alcohols comprising a fatty chain comprising, for example, from 8 to 18 carbon atoms, it being possible for the number of ethylene oxide or propylene oxide groups to range, for example, from 2 to 50 and for the number of glycerol groups to range, for example, from 2 to 30. Mention may also be made of copolymers of ethylene oxide and of propylene oxide, condensates of ethylene oxide and of propylene oxide with fatty alcohols; polyethoxylated fatty amides, for example, those comprising from 2 to 30 mol of ethylene oxide, polyglycerolated fatty amides comprising on average from 1 to 5, and such as from 1.5 to 4, glycerol groups; polyethoxylated fatty amines such as those comprising from 2 to 30 mol of ethylene oxide; oxyethylenated fatty acid esters of sorbitan comprising from 2 to 30 mol of ethylene oxide; fatty acid esters of sucrose, fatty acid esters of polyethylene glycol, alkylpolyglycosides, N-alkylglucamine derivatives, amine oxides such as ($C_{10}$-$C_{14}$)alkylamine oxides or N-acylaminopropylmorpholine oxides. It may be noted that the alkylpolyglycosides constitute nonionic surfactants that can be used in the context of the present invention.

(iii) Amphoteric surfactants:

The amphoteric surfactants can be chosen, for example, from aliphatic secondary and tertiary amine derivatives in which the aliphatic radical is chosen from linear and branched chains comprising from 8 to 22 carbon atoms and comprising at least one water-soluble anionic group (for example carboxylate, sulphonate, sulphate, phosphate or phosphonate); mention may also be made of ($C_8$-$C_{20}$)alkylbetaines, sulphobetaines, ($C_8$-$C_{20}$)alkylamido($C_1$-$C_6$)alkylbetaines or ($C_8$-$C_{20}$)alkylamido($C_1$-$C_6$)alkylsulphobetaines.

Among the ($C_8$-$C_{20}$)alkylamido($C_1$-$C_6$)alkylbetaines that may be mentioned is the cocoamidopropylbetaine sold, for example, by Goldschmidt under the name Tegobetaine F50.

Among the amine derivatives, mention may be made of the products sold under the name Mirapol, as described, for example, in U.S. Pat. Nos. 2,528,378 and 2,781,354 and having the structures of:

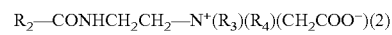

in which: $R_2$ is chosen from alkyl radicals derived from an acid $R_2$—COOH present in hydrolyzed coconut oil, and heptyl, nonyl and undecyl radicals, $R_3$ is a β-hydroxyethyl group and $R_4$ is a carboxymethyl group;

and of

wherein B represents —$CH_2CH_2OX'$, C represents —$(CH_2)_z$—Y', with z=1 or 2, X' is chosen from the —$CH_2CH_2$—COOH group and a hydrogen atom, Y' is chosen from the —COOH and the —$CH_2$—CHOH—$SO_3H$, radicals, $R_5$ is chosen from alkyl radicals of an acid $R_5$—COOH present in coconut oil or in hydrolyzed linseed oil, alkyl radicals such as $C_7$, $C_9$, $C_{11}$ and $C_{13}$ alkyl radicals, a $C_{17}$ alkyl radical and its iso form, and an unsaturated $C_{17}$ radical.

These compounds are classified in the CTFA dictionary, 5th edition, 1993, under the names disodium cocoamphodiacetate, disodium lauroamphodiacetate, disodium caprylamphodiacetate, disodium capryloamphodiacetate, disodium cocoamphodipropionate, disodium lauroamphodipropionate, disodium caprylamphodipropionate, disodium caprylloamphodipropionate, lauroamphodipropionate acid, and cocoamphodipropionic acid.

By way of example, mention may be made of the cocoamphodiacetate sold under the trade name Mirapol C2M concentrated by the company Rhodia Chimie.

(iv) The cationic surfactants may be chosen from:

A)—the quaternary ammonium salts of general formula (XIII) below:

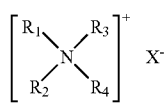 (XIII)

wherein $X^-$ is an anion chosen from halides (chloride, bromide and iodide), ($C_2$-$C_6$)alkyl sulphates, such as methyl sulphate, phosphates, alkyl and alkylaryl sulphonates, and anions derived from organic acids, such as acetate and lactate, and a) the radicals $R_1$ to $R_3$, which may be identical or different, are chosen from linear and branched aliphatic radicals comprising from 1 to 4 carbon atoms, and aromatic radicals such as aryl and alkylaryl. The aliphatic radicals can comprise at least one hetero atom such as, oxygen, nitrogen, sulphur and halogen. The aliphatic radicals are chosen, for example, from alkyl, alkoxy and alkylamide radicals, $R_4$ is chosen from linear and branched alkyl radicals comprising from 16 to 30 carbon atoms.

The cationic surfactant is, for example, a behenyltrimethylammonium salt (for example chloride).

b) the radicals $R_1$ and $R_2$, which may be identical or different, are chosen from linear and branched aliphatic radicals comprising from 1 to 4 carbon atoms, and aromatic radicals such as aryl and alkylaryl. The aliphatic radicals can comprise at least one hetero atom such as oxygen, nitrogen, sulphur and halogen. The aliphatic radicals are chosen, for example, from alkyl, alkoxy, alkylamide and hydroxyalkyl radicals comprising from about 1 to 4 carbon atoms;

$R_3$ and $R_4$, which may be identical or different, are chosen from linear and branched alkyl radicals comprising from 12 to 30 carbon atoms, the alkyl radicals may comprise at least one ester or amide function.

$R_3$ and $R_4$ are chosen, for example, from ($C_{12}$-$C_{22}$)alkylamido($C_2$-$C_6$)alkyl and ($C_{12}$-$C_{22}$)alkylacetate radicals.

The cationic surfactant is, for example, a stearamidopropyldimethyl(myristyl acetate)ammonium salt (for example chloride);

B)—the quaternary ammonium salts of imidazolinium, such as that of formula (XIV) below:

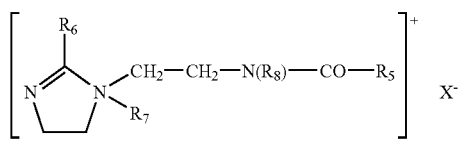 (XIV)

in which $R_5$ is chosen from alkenyl and alkyl radicals comprising from 8 to 30 carbon atoms, for example fatty acid derivatives of tallow, $R_6$ is chosen from a hydrogen atom, $C_1$-$C_4$ alkyl radicals and alkenyl and alkyl radicals comprising from 8 to 30 carbon atoms, $R_7$ is chosen from $C_1$-$C_4$ alkyl radicals, $R_8$ is chosen from a hydrogen atom and $C_1$-$C_4$ alkyl radicals, and $X^-$ is an anion chosen from halides, phosphates, acetates, lactates, alkyl sulphates, alkyl sulphonates and alkylaryl sulphonates.

In one embodiment, $R_5$ and $R_6$ are, for example, a mixture of radicals chosen from alkenyl and alkyl radicals comprising from 12 to 21 carbon atoms, such as fatty acid derivatives of tallow, $R_7$ is methyl and $R_8$ is hydrogen. Such a product is, for example, Quaternium-27 (CTFA 1997) or Quaternium-83 (CTFA 1997), which are sold under the names "Rewoquat" W75, W90, W75PG and W75HPG by the company Witco, C)—the diquaternary ammonium salts of formula (XV):

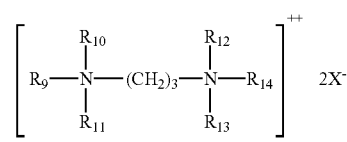 (XV)

in which $R_9$ is chosen from aliphatic radicals comprising from 16 to 30 carbon atoms, $R_{10}$, $R_{11}$, $R_{12}$, $R_{13}$ and $R_{14}$, which may be identical or different, are chosen from hydrogen and alkyl radicals comprising from 1 to 4 carbon atoms, and $X^-$ is an anion chosen from halides, acetates, phosphates, nitrates and methyl sulphates.

Such diquaternary ammonium salts, for example, include propanetallowdiammmonium dichloride; and D)—the quaternary ammonium salts comprising at least one ester function, of formula (XVI) below:

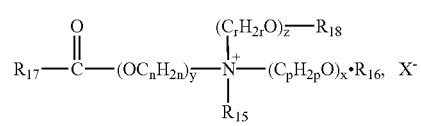 (XVI)

in which:

$R_{15}$ is chosen from $C_1$-$C_6$ alkyl radicals and $C_1$-$C_6$ hydroxyalkyl and dihydroxyalkyl radicals;

$R_{16}$ is chosen from:

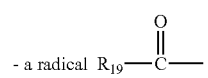

- a radical $R_{19}$—C—
$\quad\quad\quad\quad\quad\quad\parallel$
$\quad\quad\quad\quad\quad\quad$O linear and branched, saturated and unsaturated $C_1$-$C_{22}$ hydrocarbon-based radicals $R_{20}$, and a hydrogen atom, $R_{18}$ is chosen from:

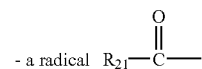

- a radical $R_{21}$—C—
$\quad\quad\quad\quad\quad\quad\parallel$
$\quad\quad\quad\quad\quad\quad$O linear and branched, saturated and unsaturated $C_1$-$C_6$ hydrocarbon-based radicals $R_{22}$, and a hydrogen atom, $R_{17}$, $R_{19}$ and $R_{21}$, which may be identical or different, are chosen from linear and branched, saturated and unsaturated $C_7$-$C_{21}$ hydrocarbon-based radicals;

n, p and r, which may be identical or different, are chosen from integers ranging from 2 to 6;

y is chosen from integers ranging from 1 to 10;

x and z, which may be identical or different, are chosen from integers ranging from 0 to 10;

X⁻ is an anion chosen from simple and complex, organic and inorganic anions;

with the proviso that the sum x+y+z is from 1 to 15, that when x is 0, then $R_{16}$ is $R_{20}$ and that when z is 0, then $R_{18}$ is $R_{22}$.

In one embodiment, the ammonium salts of formula (XVI) can be used, in which:

$R_{15}$ is chosen from methyl and ethyl radicals, x and y are equal to 1;

z is equal to 0 or 1;

n, p and r are equal to 2;

$R_{16}$ is chosen from:

- a radical $R_{19}-\overset{\overset{O}{\|}}{C}-$ methyl, ethyl and $C_{14}$-$C_{22}$ hydrocarbon-based radicals, and a hydrogen atom;

$R_{17}$, $R_{19}$ and $R_{21}$, which may be identical or different, are chosen from linear and branched, saturated and unsaturated $C_7$-$C_{21}$ hydrocarbon-based radicals;

$R_{18}$ is chosen from:

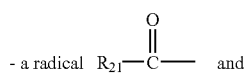
- a radical $R_{21}-\overset{\overset{O}{\|}}{C}-$ and a hydrogen atom.

Such compounds are sold, for example, under the names Dehyquart by the company Cognis, Stepanquat by the company Stepan, Noxamium by the company Ceca, and Rewoquat WE 18 by the company Rewo-Witco.

Among the quaternary ammonium salts, examples are behenyltrimethylammonium chloride and stearamidopropylmethyl(myristyl acetate)ammonium chloride, sold under the name "Ceraphyl 70" by the company Van Dyk, and Quaternium-27 or Quaternium-83 sold by the company Witco.

In the compositions in accordance with the invention, mixtures of surfactants, such as mixtures of anionic surfactants, mixtures of anionic surfactants and of at least one surfactant chosen from amphoteric, cationic and nonionic surfactants, and mixtures of cationic surfactants with at least one surfactant chosen from nonionic and amphoteric surfactants may be used. One mixture, for example, is a mixture comprising at least one anionic surfactant and of at least one amphoteric surfactant.

The composition of the invention may also comprise at least one additive chosen from thickeners, fragrances, nacreous agents, preserving agents, silicone and non-silicone sunscreens, anionic and nonionic polymers, non-cationic proteins, non-cationic protein hydrolysates, 18-methyl eicosanoic acid, hydroxy acids, vitamins, provitamins such as panthenol, silicones, antidandruff or anti-seborrhoeic agents, electrolytes, proteins, protein hydrolysates, fluoro oils or perfluoro oils, natural or synthetic waxes, compounds of ceramide type, fatty amines, fatty acids and derivatives thereof, fatty alcohols and derivatives thereof and also mixtures of these various compounds and any other additive conventionally used in cosmetics that does not affect the properties of the compositions according to the invention.

The compositions in accordance with the invention may also comprise up to 5% of nacreous or opacifying agents that are well known, such as sodium or magnesium palmitate, sodium or magnesium stearate or hydroxystearate, fatty-chain acyl derivatives such as ethylene glycol or polyethylene glycol monostearates or distearates, fatty-chain ethers, such as $C_{10}$-$C_{30}$ fatty-chain ethers, such as distearyl ether or 1-(hexadecyloxy)-2-octadecanol, and fatty alcohols, such as stearyl alcohol, cetyl alcohol or behenyl alcohol, and mixtures thereof.

These additives are optionally present in the composition according to the invention in proportions that can range from 0.001% to 20% by weight relative to the total weight of the composition. The precise amount of each additive is readily determined by a person skilled in the art on the basis of its nature and its function.

The physiologically and cosmetically acceptable medium may consist solely of water or of a mixture of water and a cosmetically acceptable solvent such as a $C_1$-$C_4$ lower alcohol, for instance ethanol, isopropanol, tert-butanol or n-butanol; alkylene glycols, for instance propylene glycol, and glycol ethers.

For example, the composition comprises from 50% to 95% by weight of water relative to the total weight of the composition, and further for example, from 60% to 90% by weight of water relative to the total weight of the composition.

The compositions according to the invention can have a final pH generally ranging from 3 to 10. For example, this pH is ranging from 4 to 8. Adjusting the pH to the desired value may be performed conventionally by adding a base (organic or mineral base) to the composition, for example aqueous ammonia or a primary, secondary or tertiary (poly) amine, for instance monoethanolamine, diethanolamine, triethanolamine, isopropanolamine or 1,3-propanediamine, or by adding a mineral or organic acid, such as a carboxylic acid, for example, citric acid.

The compositions in accordance with the invention may be used, for example, for washing or treating keratin materials such as the hair, the skin, the eyelashes, the eyebrows, the nails, the lips or the scalp.

The compositions according to the invention may be detergent compositions such as shampoos, shower gels and bubble baths. In this embodiment of the invention, the compositions comprise at least one washing base, which is generally aqueous.

The at least one washing base comprises at least one detergent surfactant. The at least one surfactant may be chosen, without discrimination, alone or as mixtures, from the anionic, amphoteric, nonionic and cationic surfactants as defined above.

In the compositions in accordance with the invention, at least one anionic surfactant or mixtures of at least one anionic surfactant and of at least one surfactant chosen from amphoteric surfactants and nonionic surfactants can be, for example, used.

In one embodiment, a mixture, for example, is a mixture comprising at least one anionic surfactant and at least one amphoteric surfactant.

For example, one can use an anionic surfactant chosen from sodium, triethanolamine and ammonium ($C_{12}$-$C_{14}$) alkyl sulphates, sodium, triethanolamine and ammonium ($C_{12}$-$C_{14}$)alkyl ether sulphates oxyethylenated with 2.2 mol of ethylene oxide, sodium cocoyl isethionate and sodium α-($C_{14}$-$C_{16}$)olefin sulphonate, and mixtures thereof with:

either an amphoteric surfactant such as the amine derivatives known as disodium cocoamphodipropionate and sodium cocoamphopropionate sold, for example, by the company Rhodia Chimie under the trade name "Mirapol C2M Conc" as an aqueous solution comprising 38% active material, or under the name Mirapol C32; or an amphoteric surfactant of zwitterionic type, such as alkylbetaines and alkylamidobetaines and, for example, the cocobetaine sold under the name "Dehyton AB 30" as an aqueous solution comprising 32% AM by the company Cognis.

Further, for example, one can use an anionic surfactant chosen from ($C_{12}$-$C_{14}$)alkyl sulfates of sodium, of triethanolamine and of ammonium, ($C_{12}$-$C_{14}$)alkyl ether sulfates of sodium, of triethanolamine and of ammonium oxyethylenated with 2.2 mol of ethylene oxide, sodium cocoyl isethionate and sodium α-($C_{14}$-$C_{16}$)olefin sulphonate and mixtures thereof with:

either an amphoteric surfactant such as the amine derivatives known as disodium cocoamphodipropionate and sodium cocoamphopropionate sold, for example, by the company Rhodia Chimie under the trade name "Mirapol C2M Conc" as an aqueous solution comprising 38% active material, or under the name Mirapol C32; or an amphoteric surfactant of zwitterionic type, such as alkylbetaines, for example, the cocobetaine sold under the name "Dehyton AB 30" as an aqueous solution comprising 32% AM by the company Cognis and the cocoamidopropylbetaine sold, for example, by Goldschmidt under the name Tegobetaine F50.

The quantity and quality of the washing base are those that are sufficient to be able to give the final composition satisfactory foaming power and/or detergent power.

These detergent compositions are, for example, foaming and the foaming power of the compositions according to the invention, characterized by a foam height, is generally greater than 75 mm, such as greater than 100 mm, measured according to the modified Ross-Miles method (NF T 73-404/IS696).

The modifications to the method are the following:

The measurement is performed at a temperature of 22° C. with osmosed water. The concentration of the solution is 2 g/l. The height of the drop is 1 m. The amount of composition that is dropped is 200 ml. These 200 ml of composition fall into a measuring cylinder 50 mm in diameter and containing 50 ml of the test composition. The measurement is taken 5 minutes after stopping the flow of the composition.

Thus, according to the invention, the washing base can be in an amount ranging from 3% to 50% by weight, such as from 6% to 35% by weight and further such as from 8% to 25% by weight relative to the total weight of the final composition.

Another aspect of the invention is a process for treating a keratin material such as the skin or the hair, characterized in that the process comprises applying to the keratin material a cosmetic composition as defined above, and then optionally rinsing it out with water.

Thus, this process according to the invention can allow the maintenance of the hairstyle and the treatment, care, washing or removal of makeup of the skin, the hair or any other keratin material.

The compositions of the invention may also be in the form of rinse-out or leave-in conditioners, permanent-waving, hair-straightening, dyeing or bleaching compositions, or in the form of rinse-out compositions to be applied before or after dyeing, bleaching, permanent-waving or straightening the hair or between the two steps of a permanent-waving or hair-straightening operation.

When the composition is in the form of a conditioner, such as a rinse-out conditioner, it, for example, comprises at least one cationic surfactant, and its concentration is generally from 0.1% to 10% by weight, and such as from 0.5% to 5% by weight relative to the total weight of the composition.

The compositions of the invention may also be in the form of washing compositions for the skin, such as in the form of bath or shower solutions or gels or makeup-removing products.

The compositions according to the invention may also be in the form of aqueous or aqueous-alcoholic lotions for skincare and/or haircare.

The cosmetic compositions according to the invention may be in the form of a gel, a milk, a cream, an emulsion, a thickened lotion or a mousse and may be used for the skin, the nails, the eyelashes, the lips and, for example, the hair.

The compositions may be packaged in various forms, such as in vaporizers, pump-dispenser bottles or in aerosol containers to allow an application of the composition in vaporized form or in the form of a mousse. Such packaging forms are indicated, for example, when it is desired to obtain a spray, a lacquer or a mousse for treating keratin materials, such as the hair.

Throughout the text hereinabove and hereinbelow, the percentages expressed are on a weight basis.

The invention will now be illustrated more fully with the aid of the examples that follow, which cannot be considered as limiting it to the embodiments described.

In the examples, AM means active material.

EXAMPLE 1

A shampoo in accordance with the invention, comprising the composition below, was prepared:

| Composition | Example | |
|---|---|---|
| Sodium lauryl ether sulphate containing 2.2 mol of ethylene oxide, as an aqueous solution containing 70% AM | 12.5 g | AM |
| Cocoylbetaine as an aqueous solution containing 30% AM | 2.4 g | AM |
| (34/24/29/10 $C_8$/$C_{10}$/$C_{12}$/$C_{14}$)alkylpolyglucoside (1,4) | 1.4 g | AM |
| Methacrylic acid/ethyl acrylate copolymer as an aqueous emulsion containing 30% active material, sold by Noveon | 1.2 g | AM |
| Avocado oil | 1 g | |
| Guar gum modified with 2,3-epoxypropyl-trimethylammonium chloride, sold under the name Jaguar C13S by the company Rhodia | 0.1 g | |
| Ethylene glycol distearate | 2 g | |
| Oxyethylenated (60 EO) cetylstearyl myristyl glycol ether | 1.5 g | |
| Preserving agents | q.s. | |
| Citric acid or sodium hydroxide | q.s. pH 5.5 | |
| Demineralized water q.s. | 100 g | |

The composition is stable at least one week at an ambient temperature (about 20-25° C.). Moistened hair is not laden and is easy to shape.

What is claimed is:

1. A cosmetic composition comprising, in a cosmetically acceptable medium,
    at least one crosslinked copolymer of methacrylic acid and of a $C_1$-$C_4$ alkyl acrylate,
    at least one plant oil with a palmitoleic acid content of greater than or equal to 0.2% by weight of the oil, wherein the plant oils are chosen from avocado oils, jojoba oils, olive oils, apricot oils and transesterified oils, and at least one cationic polysaccharide chosen from guar gums modified with a 2,3-epoxypropyltrimethylammonium salt and from hydroxyethylcelluloses that have reacted with an epoxide substituted with a trimethylammonium group.

2. The composition according to claim 1, characterized in that, in the at least one crosslinked copolymer, the methacrylic acid residue is in an amount ranging from 20% to 80% by weight relative to the total weight of the copolymer.

3. The composition according to claim 2, characterized in that, in the at least one crosslinked copolymer, the methacrylic acid residue is in an amount ranging from 25% to 70% by weight relative to the total weight of the copolymer.

4. The composition according to claim 3, characterized in that, in the at least one crosslinked copolymer, the methacrylic acid residue is in an amount ranging from 35% to 60% by weight relative to the total weight of the copolymer.

5. The composition according to claim 1, characterized in that, in the at least one crosslinked copolymer, the alkyl acrylate residue is in an amount ranging from 15% to 80% by weight relative to the total weight of the copolymer.

6. The composition according to claim 5, characterized in that, in the at least one crosslinked copolymer, the alkyl acrylate residue is in an amount ranging from 25% to 75% by weight relative to the total weight of the copolymer.

7. The composition according to claim 6, characterized in that, in the at least one crosslinked copolymer, the alkyl acrylate residue is in an amount ranging from 40% to 65% by weight relative to the total weight of the copolymer.

8. The composition according to claim 1, characterized in that, in the at least one crosslinked copolymer, the alkyl acrylate residue is chosen from methyl acrylate, ethyl acrylate, and butyl acrylate residues.

9. The composition according to claim 8, characterized in that the alkyl acrylate residue is ethyl acrylate residue.

10. The composition according to claim 1, wherein the at least one crosslinked copolymer of methacrylic acid and of a $C_1$-$C_4$ alkyl acrylate is crosslinked with at least one ethylenically polyunsaturated crosslinking agent.

11. The composition according to claim 10, characterized in that the content of the at least one ethylenically polyunsaturated crosslinking agent ranges from 0.01% to 5% by weight relative to the total weight of the copolymer.

12. The composition according to claim 11, characterized in that the content of the at least one ethylenically polyunsaturated crosslinking agent ranges from 0.03% to 3% by weight relative to the total weight of the copolymer.

13. The composition according to claim 12, characterized in that the content of the at least one ethylenically polyunsaturated crosslinking agent ranges from 0.05% to 1% by weight relative to the total weight of the copolymer.

14. The composition according to claim 1, characterized in that the at least one crosslinked copolymer of methacrylic acid and of a $C_1$-$C_4$ alkyl acrylate is in the form of a dispersion of particles in water.

15. The composition according to claim 14, characterized in that the number-average size of the particles of the copolymer in the dispersion ranges from 10 to 500 nm.

16. The composition according to claim 15, characterized in that the number-average size of the particles of the copolymer in the dispersion ranges from 20 to 200 nm.

17. The composition according to claim 16, characterized in that the number-average size of the particles of the copolymer in the dispersion ranges from 50 to 150 nm.

18. The composition according to claim 1, characterized in that the at least one crosslinked copolymer of methacrylic acid and of a $C_1$-$C_4$ alkyl acrylate is in a concentration ranging from 0.01% to 20% by weight relative to the total weight of the composition.

19. The composition according to claim 18, characterized in that the at least one crosslinked copolymer of methacrylic acid and of a $C_1$-$C_4$ alkyl acrylate is in a concentration ranging from 0.05% to 15% by weight relative to the total weight of the composition.

20. The composition according to claim 1, characterized in that the plant oil is in a concentration ranging from 0.001% to 20% by weight relative to the total weight of the composition.

21. The composition according to claim 20, characterized in that the plant oil is in a concentration ranging from 0.01% to 10% by weight relative to the total weight of the composition.

22. The composition according to claim 1, characterized in that the cationic polysaccharide is in a concentration ranging from 0.001% to 20% by weight relative to the total weight of the composition.

23. The composition according to claim 22, characterized in that the cationic polysaccharide is in a concentration ranging from 0.01% to 10% by weight relative to the total weight of the composition.

24. The composition according to claim 1, further comprising at least one surfactant chosen from anionic, nonionic, amphoteric and cationic surfactants.

25. The composition according to claim 24, characterized in that the at least one surfactant is chosen from anionic surfactants, mixtures of at least one anionic surfactant and at least one amphoteric surfactant, and mixtures of at least one anionic surfactant and at least one nonionic surfactant.

26. The composition according to claims 24, characterized in that the at least one surfactant is in a concentration ranging from 0.01% to 50% by weight relative to the total weight of the composition.

27. The composition according to claims 26, characterized in that the at least one surfactant is in a concentration ranging from 0.1% to 40% by weight relative to the total weight of the composition.

28. The composition according to claims 27, characterized in that the at least one surfactant is in a concentration ranging from 0.5% to 30% by weight relative to the total weight of the composition.

29. The composition according to claim 1, further comprising at least one additive chosen from thickeners, anti-dandruff agents, anti-seborrhoeic agents, fragrances, nacreous agents, hydroxy acids, electrolytes, preserving agents, silicone and non-silicone sunscreens, vitamins, provitamins, anionic and nonionic polymers, proteins, protein hydrolysates, 18-methyleicosanoic acid, fluoro and perfluoro oils, silicones, natural and synthetic waxes, compounds of ceramide type, fatty amines, fatty acids and derivatives thereof, fatty alcohols and derivatives thereof.

30. The composition according to claim 29, wherein the provitamins are chosen from panthenol.

31. The composition according to claim 1, characterized in that the composition is in the form of a shampoo, a conditioner, a permanent-waving, straightening, dyeing or bleaching composition for hair, a rinse-out composition to be applied between the two steps of a permanent-waving or hair-straightening operation, or a washing composition for a body.

32. A composition for washing or caring for a keratin material comprising, in a cosmetically acceptable medium,
at least one crosslinked copolymer of methacrylic acid and of a $C_1$-$C_4$ alkyl acrylate, and at least one plant oil with a palmitoleic acid content of greater than or equal to 0.2% by weight of the oil, wherein the plant oils are chosen from avocado oils, jojoba oils, olive oils, apricot oils and transesterified oils, and at least one cationic polysaccharide chosen from guar gums modified with a 2,3-epoxypropyltrimethylammonium salt and from hydroxyethylcelluloses that have reacted with an epoxide substituted with a trimethylammonium group, said composition being effective for washing or caring for a keratin material.

33. A method for washing or caring for a keratin material comprising applying to the keratin material a composition comprising, in a cosmetically acceptable medium, at least one crosslinked copolymer of methacrylic acid and of a $C_1$-$C_4$ alkyl acrylate, at least one plant oil with a palmitoleic acid content of greater than or equal to 0.2% by weight of the oil, wherein the plant oils are chosen from avocado oils, jojoba oils, olive oils, apricot oils and transesterified oils, and at least onecationic polysaccharide chosen from guar gums modified with a 2,3-epoxypropyltrimethylammonium salt and from hydroxyethylcelluloses that have reacted with an epoxide substituted with a trimethylammonium group.

34. A process for treating a keratin material, comprising applying to the keratin material a cosmetic composition comprising, in a cosmetically acceptable medium, at least one crosslinked copolymer of methacrylic acid and of a $C_1$-$C_4$ alkyl acrylate, at least one plant oil with a palmitoleic acid content of greater than or equal to 0.2% by weight of the oil, wherein the plant oils are chosen from avocado oils, jojoba oils, olive oils, apricot oils and transesterified oils, and at least one cationic polysaccharide chosen from guar gums modified with a 2,3-epoxypropyltrimethylammonium salt and from hydroxyethylcelluloses that have reacted with an epoxide substituted with a trimethylammonium group, and then optionally rinsing it out with water.

35. The process according to claim 34, wherein the keratin material is hair.

36. A composition comprising, in a cosmetically acceptable medium, one composition (1) comprising at least one crosslinked methacrylic acid/$C_1$-$C_4$ acrylate copolymer and another composition (2) comprising at least one plant oil with a palmitoleic acid content of greater than or equal to 0.2% by weight of the oil, wherein the plant oils are chosen from avocado oils, jojoba oils, olive oils, apricot oils and transesterified oils, and at least one cationic polysaccharide chosen from guar gums modified with a 2,3-epoxypropyltrimethylammonium salt and from hydroxyethylcelluloses that have reacted with an epoxide substituted with a trimethylammonium group.

37. A method of manufacturing a cosmetic composition, comprising including in said composition at least one crosslinked copolymer of methacrylic acid and of a $C_1$-$C_4$ alkyl acrylate, at least one plant oil with a palmitoleic acid content of greater than or equal to 0.2% by weight of the oil, wherein the plant oils are chosen from avocado oils, jojoba oils, olive oils, apricot oils, and transesterified oils, and at least one cationic polysaccharide chosen guar gums modified with a 2,3-epoxypropyltrimethylammonium salt and from hydroxyethylcelluloses that have reacted with an epoxide substituted with a trimethylammonium group.

38. A composition to give hair lightness comprising, in a cosmetically acceptable medium, at least one crosslinked copolymer of methacrylic acid and of a $C_1$-$C_4$ alkyl acrylate, at least one plant oil with a palmitoleic acid content of greater than or equal to 0.2% by weight of the oil, wherein the plant oils are chosen from avocado oils, jojoba oils, olive oils, apricot oils, and transesterified oils, and at least one cationic polysaccharide chosen from guar gums modified with a 2,3-epoxypropyltrimethylammonium salt and from hydroxyethylcelluloses that have reacted with an epoxide substituted with a trimethylammonium group, said composition being effective for giving hair lightness.

39. A method to give hair lightness, comprising applying to the hair a composition comprising, in a cosmetically acceptable medium, at least one crosslinked copolymer of methacrylic acid and of a $C_1$-$C_4$ alkyl acrylate, at least one plant oil with a palmitoleic acid content of greater than or equal to 0.2% by weight of the oil, wherein the plant oils are chosen from avocado oils, jojoba oils, olive oils, apricot oils, and transesterified oils, and at least one cationic polysaccharide chosen from guar gums modified with a 2,3-epoxypropyltrimethylammonium salt and from hydroxyethylcelluloses that have reacted with an epoxide substituted with a trimethylammonium group.

40. A composition to give hair softness comprising, in a cosmetically acceptable medium, at least one crosslinked copolymer of methacrylic acid and of a $C_1$-$C_4$ alkyl acrylate, at least one plant oil with a palmitoleic acid content of greater than or equal to 0.2% by weight of the oil, wherein the plant oils are chosen from avocado oils, jojoba oils, olive oils, apricot oils, and transesterified oils, and at least one cationic polysaccharide chosen from guar gums modified with a 2,3-epoxypropyltrimethylammonium salt and from hydroxyethylcelluloses that have reacted with an epoxide substituted with a trimethylammonium group, said composition being effective for giving hair softness.

41. A method to give hair softness, comprising applying to the hair a composition comprising, in a cosmetically acceptable medium, at least one crosslinked copolymer of methacrylic acid and of a $C_1$-$C_4$ alkyl acrylate, at least one plant oil with a palmitoleic acid content of greater than or equal to 0.2% by weight of the oil, wherein the plant oils are chosen from avocado oils, jojoba oils, olive oils, apricot oils, and transesterified oils, and at least one cationic polysaccharide chosen from guar gums modified with a 2,3-epoxypropyltrimethylammonium salt and from hydroxyethylcelluloses that have reacted with an epoxide substituted with a trimethylammonium group.

42. A composition to give hair a smooth feel comprising, in a cosmetically acceptable medium, at least one crosslinked copolymer of methacrylic acid and of a $C_1$-$C_4$ alkyl acrylate, at least one plant oil with a palmitoleic acid content of greater than or equal to 0.2% by weight of the oil, wherein the plant oils are chosen from avocado oils, jojoba oils, olive oils, apricot oils, and transesterified oils, and at least one cationic polysaccharide chosen from guar gums modified with a 2,3-epoxypropyltrimethylammonium salt and from hydroxyethylcelluloses that have reacted with an epoxide substituted with a trimethylammonium group, said composition being effective for giving hair a smooth feel.

43. A method to give hair a smooth feel, comprising applying to the hair a composition comprising, in a cosmetically acceptable medium, at least one crosslinked copolymer of methacrylic acid and of a $C_1$-$C_4$ alkyl acrylate, at least one plant oil with a palmitoleic acid content of greater than or equal to 0.2% by weight of the oil, wherein the plant oils are chosen from avocado oils, jojoba oils, olive oils, apricot oils, and transesterified oils, and at least one cationic polysaccharide chosen from guar gums modified with a 2,3-epoxypropyltrimethylammonium salt and from hydroxyethylcelluloses that have reacted with an epoxide substituted with a trimethylammonium group.

44. A composition to give hair flexibility comprising, in a cosmetically acceptable medium, at least one crosslinked copolymer of methacrylic acid and of a $C_1$-$C_4$ alkyl acrylate, at least one plant oil with a palmitoleic acid content of greater than or equal to 0.2% by weight of the oil, wherein the plant oils are chosen from avocado oils, jojoba oils, olive oils, apricot oils, and transesterified oils, and at least one cationic polysaccharide chosen from guar gums modified with a 2,3-epoxypropyltrimethylammonium salt and from hydroxyethylcelluloses that have reacted with an epoxide substituted with a trimethylammonium group, said composition being effective for giving hair flexibility.

45. A method to give hair flexibility, comprising applying to the hair a composition comprising, in a cosmetically acceptable medium, at least one crosslinked copolymer of methacrylic acid and of a $C_1$-$C_4$ alkyl acrylate, at least one plant oil with a palmitoleic acid content of greater than or equal to 0.2% by weight of the oil, wherein the plant oils are chosen from avocado oils, jojoba oils, olive oils, apricot oils, and transesterified oils, and at least one cationic polysaccharide chosen from guar gums modified with a 2,3-epoxypropyltrimethylammonium salt and from hydroxyethylcelluloses that have reacted with an epoxide substituted with a trimethylammonium group.

46. A cosmetic composition comprising, in a cosmetically acceptable medium, at least one crosslinked copolymer of methacrylic acid and of a $C_1$-$C_4$ alkyl acrylate, at least one plant oil with a palmitoleic acid content of greater than or equal to 0.2% by weight of the oil, wherein the plant oils are chosen from avocado oils, jojoba oils, olive oils, apricot oils, and transesterified oils, and at least one cationic polysaccharide chosen from guar gums modified with a 2,3-epoxypropyltrimethylammonium salt and from hydroxyethylcelluloses that have reacted with an epoxide substituted with a trimethylammonium group, wherein the at least one crosslinked copolymer of methacrylic acid and of a $C_1$-$C_4$ alkyl acrylate is in the form of a dispersion of particles in water, and that the number-average size of the particles of the copolymer in the dispersion ranges from 10 to 500 nm.

\* \* \* \* \*

UNITED STATES PATENT AND TRADEMARK OFFICE
CERTIFICATE OF CORRECTION

PATENT NO. : 7,258,852 B2  Page 1 of 1
APPLICATION NO. : 10/237666
DATED : August 21, 2007
INVENTOR(S) : Mireille Maubru It is certified that error appears in the above-identified patent and that said Letters Patent is hereby corrected as shown below:

In claim 26, column 24, line 33, "claims" should read --claim--.

In claim 27, column 24, line 37, "claims" should read --claim--.

In claim 28, column 24, line 41, "claims" should read --claim--.

In claim 33, column 25, line 23, "onecationic" should read --one cationic--.

Signed and Sealed this

Twentieth Day of November, 2007

JON W. DUDAS
*Director of the United States Patent and Trademark Office*